United States Patent
Agren (10) Patent No.: US 7,820,042 B2
(45) Date of Patent: Oct. 26, 2010

(54) METHOD FOR REMOVING AIR FROM A CHROMATOGRAPHY COLUMN

(75) Inventor: Tomas Agren, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 73 days.

(21) Appl. No.: 12/357,426

(22) Filed: Jan. 22, 2009

(65) Prior Publication Data

US 2009/0184052 A1  Jul. 23, 2009

(30) Foreign Application Priority Data

Jan. 22, 2008 (GB) .................. 0801127.2

(51) Int. Cl.
*B01D 15/08* (2006.01)
(52) U.S. Cl. .............. 210/198.2; 210/188; 210/656
(58) Field of Classification Search .............. 210/656, 210/659, 188, 198.2, 456
See application file for complete search history.

(56) References Cited

U.S. PATENT DOCUMENTS

| | | | | |
|---|---|---|---|---|
| 2,708,519 A | * | 5/1955 | Novak | 210/269 |
| 3,487,938 A | * | 1/1970 | Patterson | 210/198.2 |
| 3,510,271 A | * | 5/1970 | Emneus et al. | 210/635 |
| 4,155,846 A | * | 5/1979 | Novak et al. | 210/659 |
| 4,361,482 A | * | 11/1982 | Teetz et al. | 210/198.2 |
| 4,382,000 A | * | 5/1983 | Wisebaker et al. | 210/638 |
| 4,384,958 A | * | 5/1983 | Wisebaker et al. | 210/638 |
| 4,676,898 A | * | 6/1987 | Saxena | 210/198.2 |
| 4,797,209 A | * | 1/1989 | Jackson | 210/656 |
| 4,840,730 A | * | 6/1989 | Saxena | 210/198.2 |
| 4,891,133 A | * | 1/1990 | Colvin, Jr. | 210/198.2 |
| 5,112,492 A | * | 5/1992 | Ransohoff | 210/656 |
| 5,141,635 A | * | 8/1992 | LePlang et al. | 210/198.2 |
| 5,186,826 A | * | 2/1993 | Otto et al. | 210/198.2 |
| 5,266,193 A | * | 11/1993 | Kimura et al. | 210/198.2 |
| 5,366,621 A | * | 11/1994 | Bidell et al. | 210/198.2 |
| 5,462,659 A | * | 10/1995 | Saxena et al. | 210/198.2 |
| 5,607,581 A | * | 3/1997 | Gerner et al. | 210/198.2 |
| 5,667,676 A | * | 9/1997 | Alaska | 210/198.2 |
| 6,139,732 A | * | 10/2000 | Pelletier | 210/198.2 |
| 6,319,398 B1 | * | 11/2001 | Saitoh | 210/198.2 |
| 6,440,301 B1 | * | 8/2002 | Dobos | 210/198.2 |
| 6,444,122 B1 | * | 9/2002 | Van Davelaar | 210/198.2 |
| 2007/0199899 A1 | * | 8/2007 | Alaska | 210/659 |

FOREIGN PATENT DOCUMENTS

| | | |
|---|---|---|
| WO | WO 99/25451 | 5/1999 |
| WO | WO 2006/083220 | 8/2006 |

* cited by examiner

*Primary Examiner*—Ernest G Therkorn
(74) *Attorney, Agent, or Firm*—Yonggang Ji (57) ABSTRACT

The invention relates to a method for removing air from the bed space of a chromatography column. The method involves use a chromatography column having an inner wall which comprises at least one elongated groove through which air can pass from the bed space to a chamber above an adapter assembly.

14 Claims, 7 Drawing Sheets

METHOD FOR REMOVING AIR FROM A CHROMATOGRAPHY COLUMN

FIELD OF THE INVENTION

The present invention relates to column chromatography and in particular to a method for removing air trapped within the bed space of a chromatography column.

BACKGROUND OF THE INVENTION

Chromatography columns provide a means for separating, purifying and isolating chemical and biological compounds. The size and type of column used in these operations typically depends upon the scale of the process in question, small glass or plastic walled columns typically being used for research purposes, while larger metal columns are employed for industrial processes. For instance, chromatography columns may be used in manufacturing processes to purify process liquids and separate substances of interest from such liquids; typical examples include large-scale preparative purification of fine chemicals and pharmaceuticals, together with biological products.

Whilst the present invention relates to both plastic walled and larger metal walled chromatography columns, it is particularly useful for manufacturing and industrial-scale chromatography columns. Industrial-scale chromatography columns typically comprise a hollow, axially vertical tubular housing including a liquid inlet at the upper end and through which the buffer and substances to be separated are dispensed to the media bed located within the cavity of the tube, and a liquid collecting system at the lower end for collecting substances and buffer. The particulate chromatographic media or bed through which the buffer fluid and/or substances to be separated and purified percolates is located between the liquid inlet and collecting system.

An adapter assembly is typically affixed to the upper end of the tubular housing and a base assembly to the lower end where it is bolted to the bottom flanges. Each of these assemblies typically comprises a strong backing plate and a distributor plate which further supports a bed support; a bed support is a layer of mesh, screen, filter, sinter or other fluid-permeable media-retaining material which permits process liquid flow into and out of the chromatography bed space or cavity while retaining the bed of particulate medium. To provide adjustability and control of the bed height and bed compression, the adapter assembly is typically made in the form of a piston or sliding adapter in the column tube interior. After the column is charged with bed media, typically through a valve or nozzle, the adapter may be forced toward the bottom of the tube to compress or pressurize the media bed. Generally the base assembly is a fixed structure which is bolted against the bottom flange of the column tube but, in some instances, may also be in the form of a movably slidable piston or adapter.

The backing plate of the base assembly generally acts as a support for the column, being itself supported on legs or some other stand arrangement, which allows clearance for outlet pipework projecting beneath the base assembly.

Liquid chromatography is a technique for separating the individual compounds that exist in a sample. In employing the technique, the sample is dissolved and carried in a liquid, called a mobile phase. The mobile phase carrying the sample is forced to migrate through a bed of particulate media, sometimes called a stationary phase. Different compounds will have differing rates of migration through the media, which effects the separation of the components in the sample. The bed of particulate media is formed under gravity, washing with a mobile phase, and/or by compression by an adapter or piston. Before a column can be used to separate compounds by liquid chromatography it is necessary to remove air from the bed space which has become trapped in the column otherwise the air will interfere with the separation process. The air may have been originally present in the bed space itself or have moved into the bed space from associated tubing, pumps or column components such as a bed support. Problems are often encountered in trying to remove the air from the column prior to conducting liquid chromatography. The trapped air may create air pockets in the stationary phase where chemical interaction between the sample and the media cannot take place. These air pockets thus negatively affect the separation of the different components in the sample.

SUMMARY OF THE INVENTION

According to a first aspect of the invention, there is provided a chromatography column comprising:
 a housing comprising an elongated tubular side wall having an inner wall;
 an adapter assembly and a base assembly axially opposed to each other, wherein the adapter assembly is axially movable by drive means relative to the base assembly;
 the adapter assembly and the base assembly together with the inner wall defining an enclosed bed space for containing a bed of particulate media therein, the adapter assembly and the inner wall defining a chamber;
 the adapter assembly further comprising a sealing assembly around the circumference thereof, the sealing assembly providing a fluid tight seal between the inner wall and the circumference of the adapter assembly;
 wherein the inner wall comprises at least one elongated groove for receipt of air or fluid present within the bed space.

In one aspect, the elongated groove is a continuous groove around the circumference of the inner wall.

In another aspect, the column comprises a plurality of elongated grooves radially spaced around the circumference of the inner wall. Preferably, the plurality of elongated grooves each has rounded edges.

In one aspect, the elongated groove has a depth within the range of 0.1 mm to 5 mm. Preferably, the depth is 0.5 mm.

In another aspect, the elongated groove has a length within the range of 10 mm to 50 mm. Preferably the length is 35 mm.

In one aspect, the elongated groove has a width within the range of 1 mm to 15 mm. Preferably, the width is 5 mm.

The groove may be vertically aligned along the axis of the column. Alternatively, the groove is acutely or obtusely angled relative to the vertical axis of the column. Preferably, one end of a first groove radially overlaps with the other end of a second groove.

The sealing assembly may take any appropriate shape or configuration (e.g. rectangular, ovoid, cuboid). Further, the sealing assembly may comprise several component parts (e.g. one or more seals). Preferably, the sealing assembly comprises an o-ring.

The drive means is selected from the group consisting of electrical motor, hydraulic pump and pneumatic pump.

The column wall may be made of any suitable material, which can withstand the operating pressures and is chemically resistant to materials to be separated on the column. Preferably, the column wall is made of stainless steel.

In a second aspect of the present invention, there is provided a method for removing air from a chromatography column, the column comprising:

a housing comprising an elongated tubular side wall having an inner wall;

an adapter assembly and a base assembly axially opposed to each other, wherein said adapter assembly is axially movable by drive means relative to the base assembly;

the adapter assembly and the base assembly together with the inner wall defining an enclosed bed space for containing a bed of particulate media therein, the adapter assembly and the inner wall defining a chamber;

the adapter assembly further comprising a sealing assembly around the circumference thereof, the sealing assembly providing a fluid tight seal between the inner wall and the circumference of the adapter assembly;

wherein the inner wall comprises at least one elongated groove, the method comprising the steps of:
a) filling the bed space with a bed of particulate media and/or liquid to at least a level above the lowest point of said groove;
b) axially moving the adapter assembly to a first position where the sealing assembly aligns with the groove to bring the bed space into fluid communication with the chamber and thereby allow air to pass from the bed space to the chamber;
c) axially moving the adapter assembly to a second position where the sealing assembly aligns with the groove and the bed space remains in fluid communication with the chamber to pressurise the bed space and thereby force air from the bed space into the chamber; and/or
d) pumping a liquid from the base assembly or the adapter assembly into the bed space to force air from the bed space into the chamber.

In one aspect, the method additionally comprises the step of axially moving the adapter assembly to a third position where the sealing assembly and the groove no longer align and air cannot pass between the bed space and the chamber.

DETAILED DESCRIPTION OF THE INVENTION

Figure 1A:
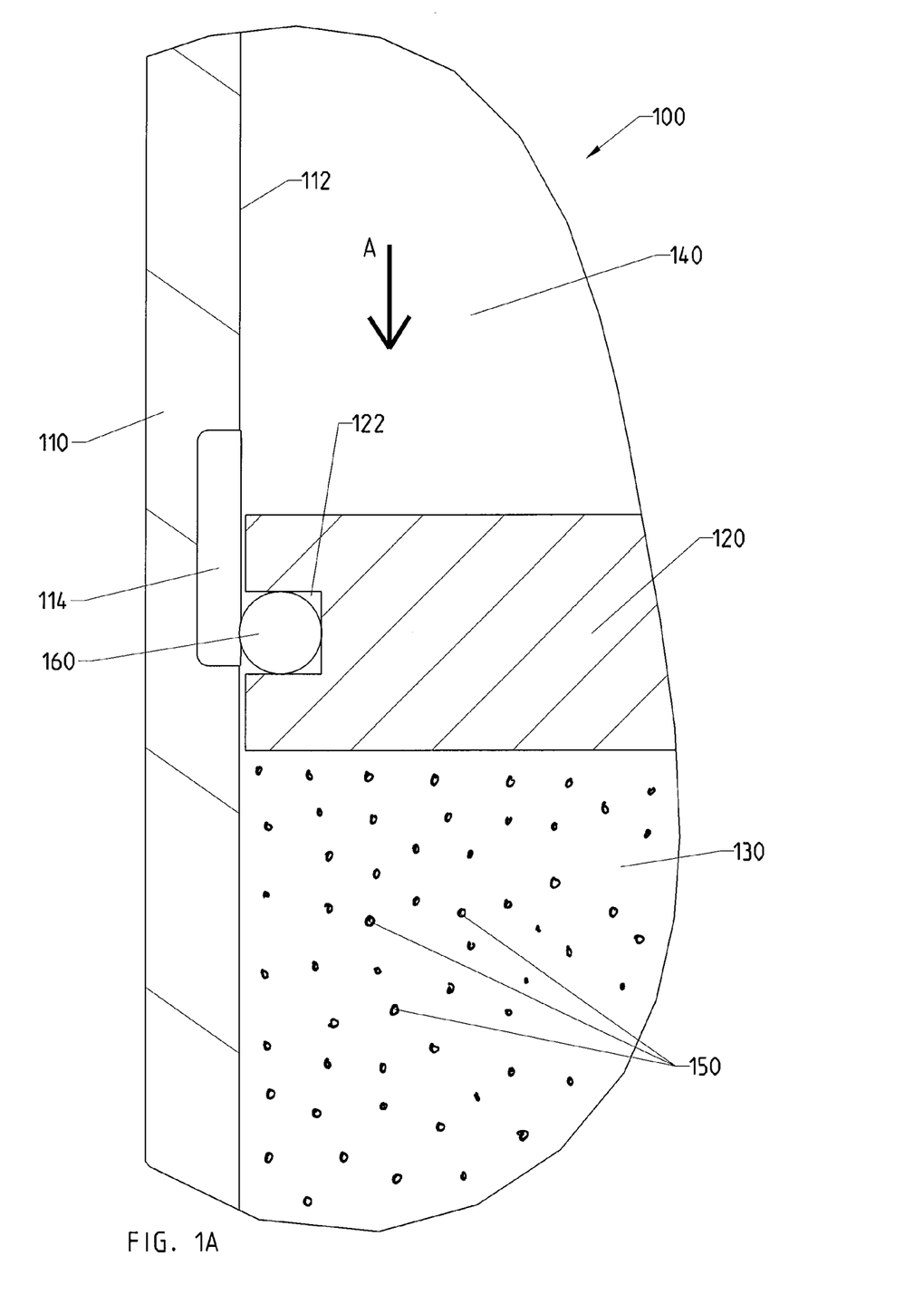
FIG. 1A is a schematic diagram showing a longitudinal cross-sectional view of part of a chromatography column according to the invention.
Figure 1B:
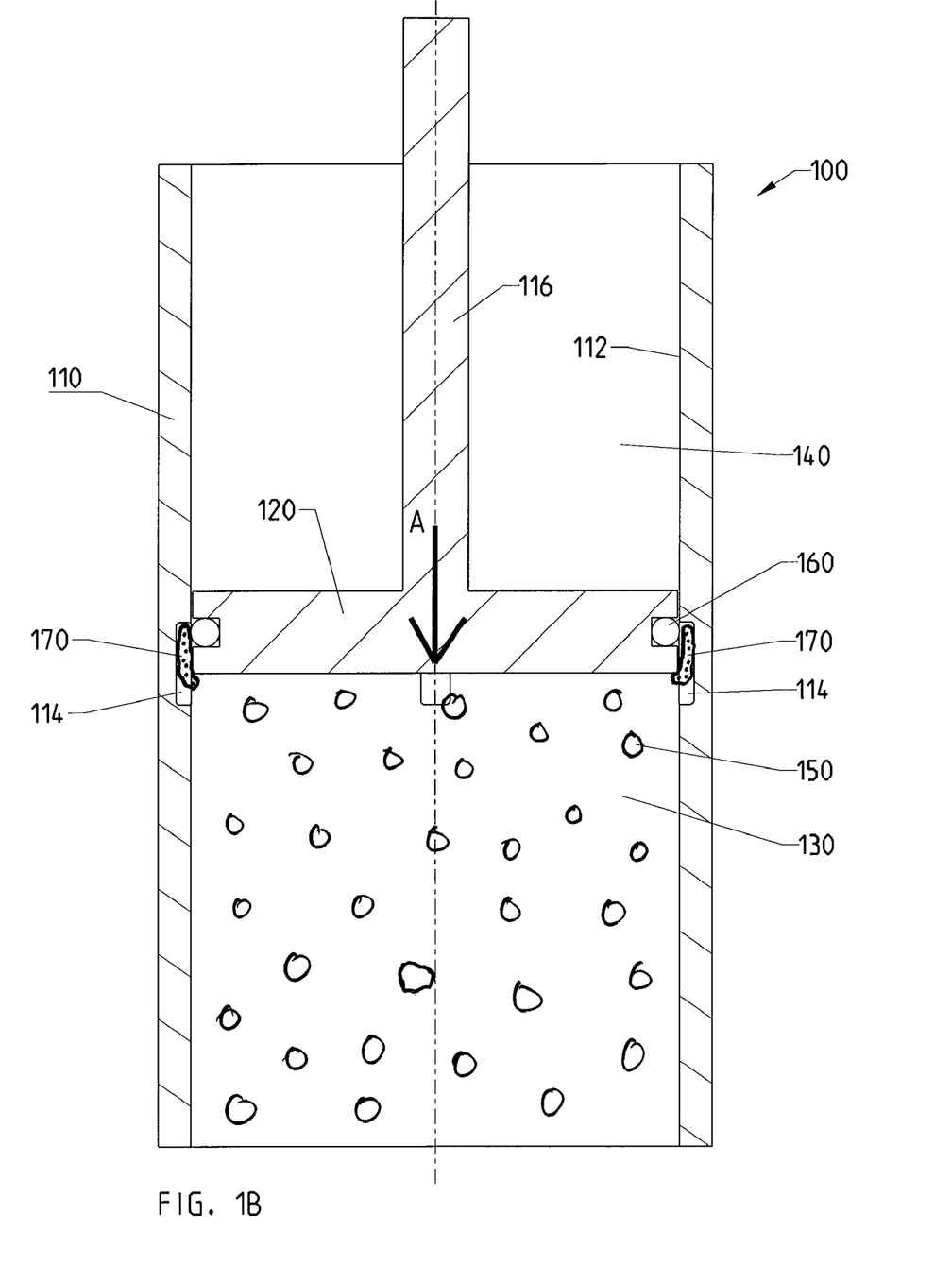
FIG. 1B is a longitudinal cross-sectional view of part of a chromatography column according to the invention showing the sealing assembly of the adapter assembly aligned in a first position with the air groove.
Figure 1C:
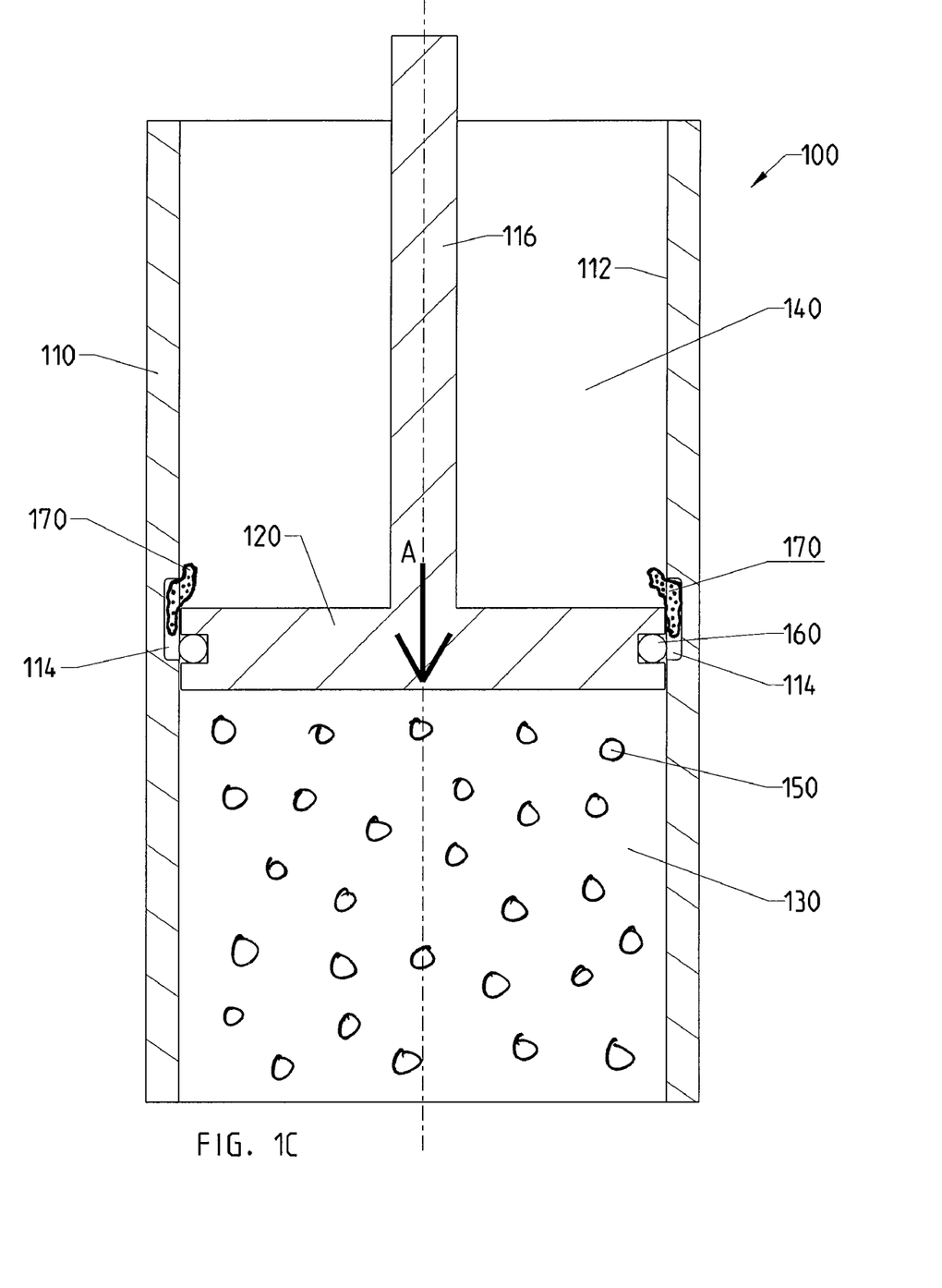
FIG. 1C is a longitudinal cross-sectional view of part of a chromatography column according to the invention showing the sealing assembly of the adapter assembly aligned in a second position with the air groove.

FIGS. 1A, B and C are schematic diagrams showing longitudinal cross-sectional views of a part of a column in accordance with the invention, with each figure depicting an adapter assembly aligned at a different position relative to an air groove in the column wall.

FIG. 1A is a schematic diagram of a cross-sectional view of part of a chromatography column 100 in accordance with the invention having an elongated tubular side wall 110 and an adapter assembly 120. Material for the tubular wall 110 is selected for properties desirable to the chromatography column application, for example, hardness, stiffness, toughness, chemical erosion resistance, deformability, formability and inexpensiveness. Suitable materials for forming the column wall 110 include plastic, metal or a suitable composite material. Plastic materials exhibiting some or all of the desired mechanical properties include polypropylene, polyethylene, acetal (also known as DELRIN) and polycarbonate. Fluoropolymers, such as PTFE, EFEP or TEFLON™, with thicker walls to achieve the required hoop strength can be used due to their chemical inertness. These materials also have the advantages of being self-lubricating; lowering the friction caused by the movement of the adapter 120 and prolonging the product life cycle. Suitable metals include stainless steel, steel alloys, aluminium and anodized aluminium as they are all chemically inert and have suitable mechanical properties, being particularly suitable for operation at high pressures.

The adapter assembly 120 is a cylindrical disc type structure that operates by moving axially inside the centre of the column walls 110 in the direction of arrow A. The disc circumference is such that it fits almost flush with the face of inner wall 112. The adapter assembly 120 effectively divides the interior of the column into two regions, a lower region or bed/media space 130 and an upper region or chamber 140. The bed/media space 130, which is further defined by a base assembly (not shown) and column walls (not shown), is designed to contain a bed of particulate media 150 suspended in a liquid carrier. A suitable material for the adapter assembly 120 must comply with all of the needs for that of the column walls 110, in that it must not only have sound mechanical properties, but also be chemically inert. Suitable materials include the fluoropolymers as they fulfil both the chemical resistance required and are self-lubricating. Metals, which are chemically inert, such as stainless steel, are particularly suitable.

The adapter assembly 120 is used to settle the bed of particulate media, which is initially in the form of a slurry, by pushing down on it; the assembly may subsequently be used to compress and pack the particulate media to achieve a packed bed suitable for chromatographic separation. The volume of the media bed 150 decreases as the adapter 120 is pushed down the column 100 (i.e. in the direction of arrow A in FIG. 1A) forcing the liquid carrier through the particulate media 150 and out of the column via a port in the base plate (not shown) or the adapter assembly 120.

In order to fully confine the carrier liquid and the particulate media it must be ensured that the solution cannot pass through the adapter assembly 120. A sealing assembly, such as o-ring 160, located within a recess 122 in the circumference of the adapter 120 is used to form a dynamic seal between the adapter assembly 120 and the inner wall 112. The o-ring 160 is made from a suitable material such that it can deform to fit tightly around the adapter 120 and create a fluid-tight tight seal with the column wall 112. O-ring 160 must also be highly durable due to the constant frictional forces acting upon it from movement against the column wall 110. A suitable material for this application is TEFLON™ coated rubber or TEFLON™ coated silicon due to its appropriate mechanical properties, long life span and low coefficient of friction.

A vertically orientated slot or groove 114 is shown in the column wall 110 in line with the adapter assembly 120. The elongated groove 114 is approximately 35 mm in length and has a width of 5 mm and depth of approximately 0.5 mm, having bevelled or rounded edges and interior surfaces to facilitate air movement into and out of the groove.

When the o-ring 160 is positioned as shown in FIG. 1A, the bed space 130 is in fluid communication with the chamber 140 and air is free to pass from the bed space 130 via groove 114 into the chamber 140. This process is described in more detail below.

FIG. 1B is a longitudinal cross section of a part of a column in accordance with the invention showing greater detail of the component parts of the column of FIG. 1A (the numbering in the figure corresponds to that of FIG. 1A) The figure depicts the axial movement of the adapter assembly 120 within the column 100 (in the direction of the arrow A) to bring the sealing assembly 160 into alignment with the groove 114 and the bed space 130 into fluid communication with the chamber 140. Any air present in the bed space can now pass freely into the chamber 140 via the groove 114. Shaft 116, which is connected to a suitable drive mechanism such as an electric motor or hydraulic pump, is used to raise or lower the adapter assembly 120 within the bed space 130.

FIG. 1C shows the vertical translation of the adapter assembly 120 from a first position depicted in FIG. 1B to a second position; the movement of the adapter assembly 120 pressurises the bed space 130. In this position, the bed space 130 is still in fluid communication with the chamber 140 via groove 114. Pressurisation of the bed space 130 forces air 170 in the bed space 130 and in groove 114 to pass or move into the chamber 140 where it can no longer interfere with chromatographic separation taking place in the bed of particulate media.

As an alternative means of forcing air from the bed space 130 through the groove 114 into the chamber, liquid (e.g. a carrier liquid) can be pumped from the base assembly (not shown) through the media bed or through the inlet of the adapter.

This process of forcing air out from the bed space 130 via groove 114 can in one embodiment of the invention be performed when the bed space 130 is filled with a slurry of particulate media. In another embodiment of the invention this step of forcing air out from the bed space is performed in a previous step where the bed space 130 is filled with a liquid, here called a priming liquid, for the purpose of priming air out of the bed space. This priming liquid could be a packing buffer for example ethanol, water or a salt buffer. The bed space is then filled with the priming liquid to at least a level above the lowest point of said groove and any air present in the bed space is forced out via the groove 114 by moving the adapter and/or pumping more liquid according to the description above. Thereafter the adapter can be pressed down, and a slurry of particulate media can instead be provided into the bed space through a dedicated inlet. The intention is to all the time keep the bed space free from air.

Figure 2A:
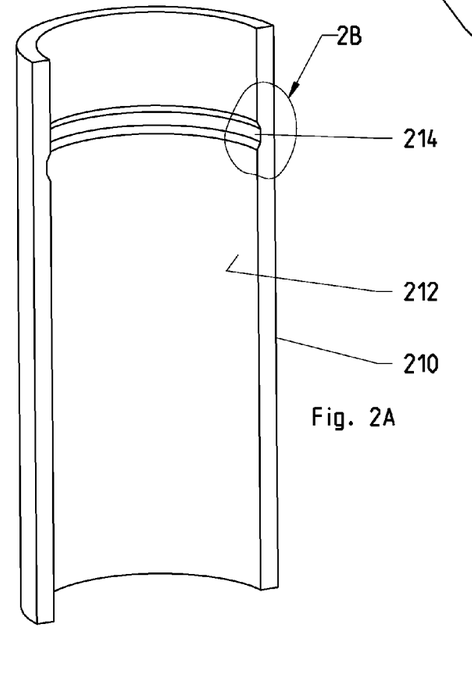
FIG. 2A is a longitudinal cross-sectional view of part of a chromatography column in accordance with the invention having one continuous radial groove in the inner column wall.

FIG. 2A is a longitudinal cross sectional view of a part of a tubular side wall 210 of a column according to the invention, showing an air groove 214 in the form of a continuous groove around the internal circumference of inner wall 212. The length and depth of groove 214 is identical to that of the discrete groove 114 described in FIG. 1 (i.e. 35 mm in length and depth of approximately 0.5 mm) with the width being the same as the internal circumference of the column.

The function of the continuous groove 214 is to allow trapped air to pass from the bed space to the chamber (not shown) when the two compartments are brought into fluid communication via the groove 214. The greater volume of the continuous groove 214 makes it capable of expelling or transferring a larger amount of trapped air from the bed space to the chamber.

Figure 2B:
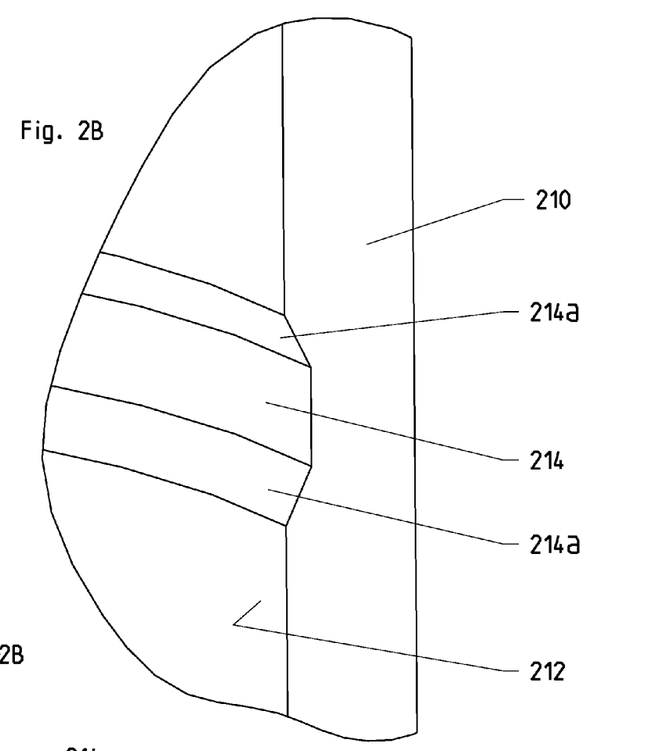
FIG. 2B is an enlarged view of area A of FIG. 2A.

FIG. 2B is an enlarged view of area A of FIG. 2A showing the continuous groove 214 in the inner wall 212 of the column wall 210. The bevelled edges or sides 214a of the groove 214 are clearly seen in the inset. The function of the bevelled edges 214a (and the smooth interior surface of the groove) is to facilitate air movement into and out of the groove.

Figures 3A, 3B:
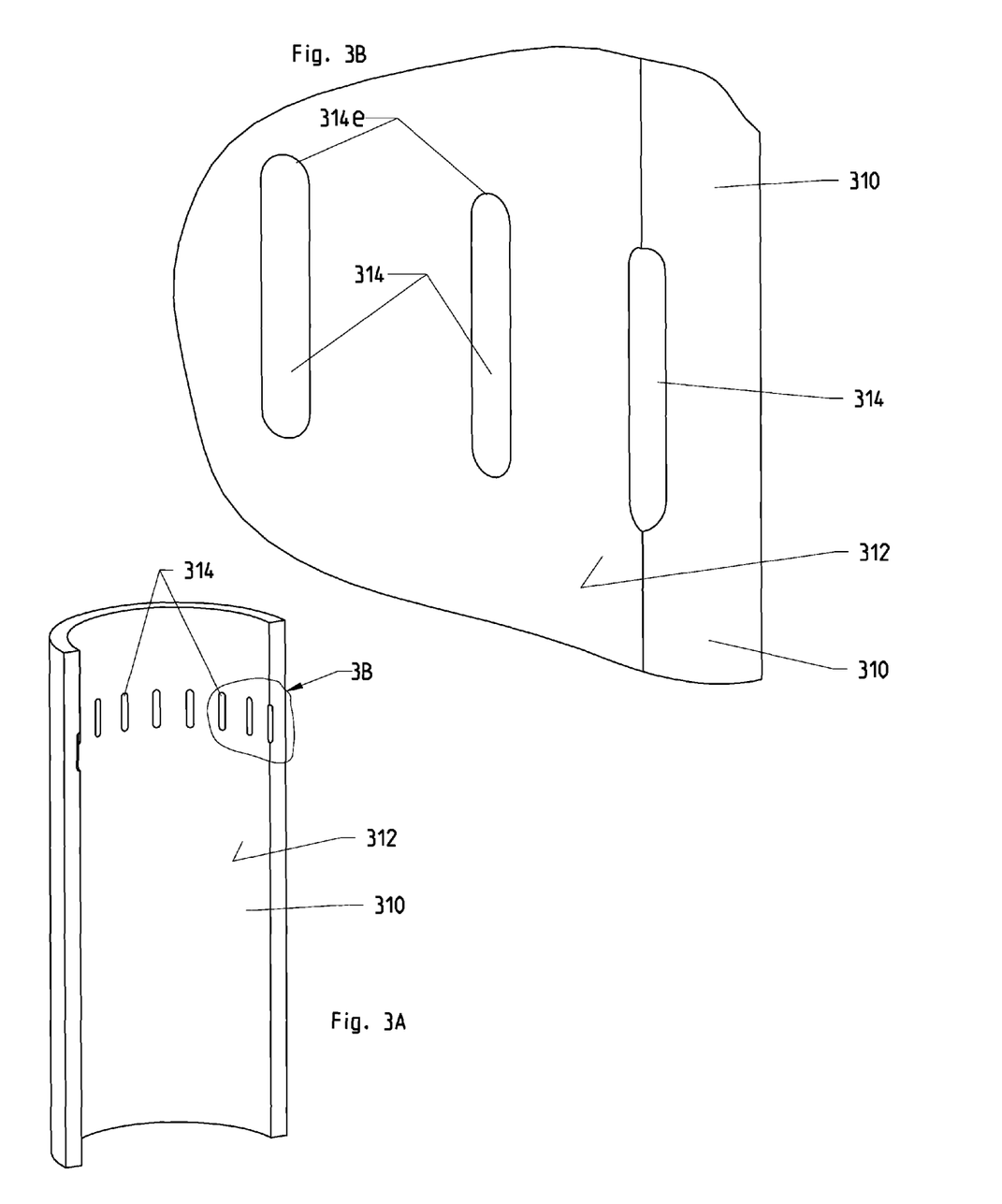
FIG. 3A is a longitudinal cross-sectional view of part of a chromatography column in accordance with the invention having vertical air grooves in the inner column wall.
FIG. 3B is an enlarged view of area A of FIG. 3A.

FIG. 3A is a longitudinal cross sectional view of a part of a tubular side wall 310 of a column according to the invention, showing a number of discrete air grooves 314. FIG. 3B is an enlarged view of the inset A of FIG. 3A. As can be seen, the air groove takes the form of discrete, axially or vertically orientated air grooves 314 positioned around the circumference of the column which act to allow the passage of air from the bed space to the chamber of the column (as described for FIG. 1 above). The air grooves 314 are equally spaced around the circumference of inner wall 312 of column wall 310 but it will be understood that they may also be spaced out varying intervals and in greater numbers than illustrated. The grooves have similar dimensions to those described in FIG. 1, being approximately 35 mm in length, 5 mm in width and having a depth of approximately 0.5 mm. The grooves 314 have bevelled or rounded edges or ends 314e (see FIG. 3B) and smooth interior surfaces to facilitate air movement into and out of the groove.

Figures 4A, 4B:
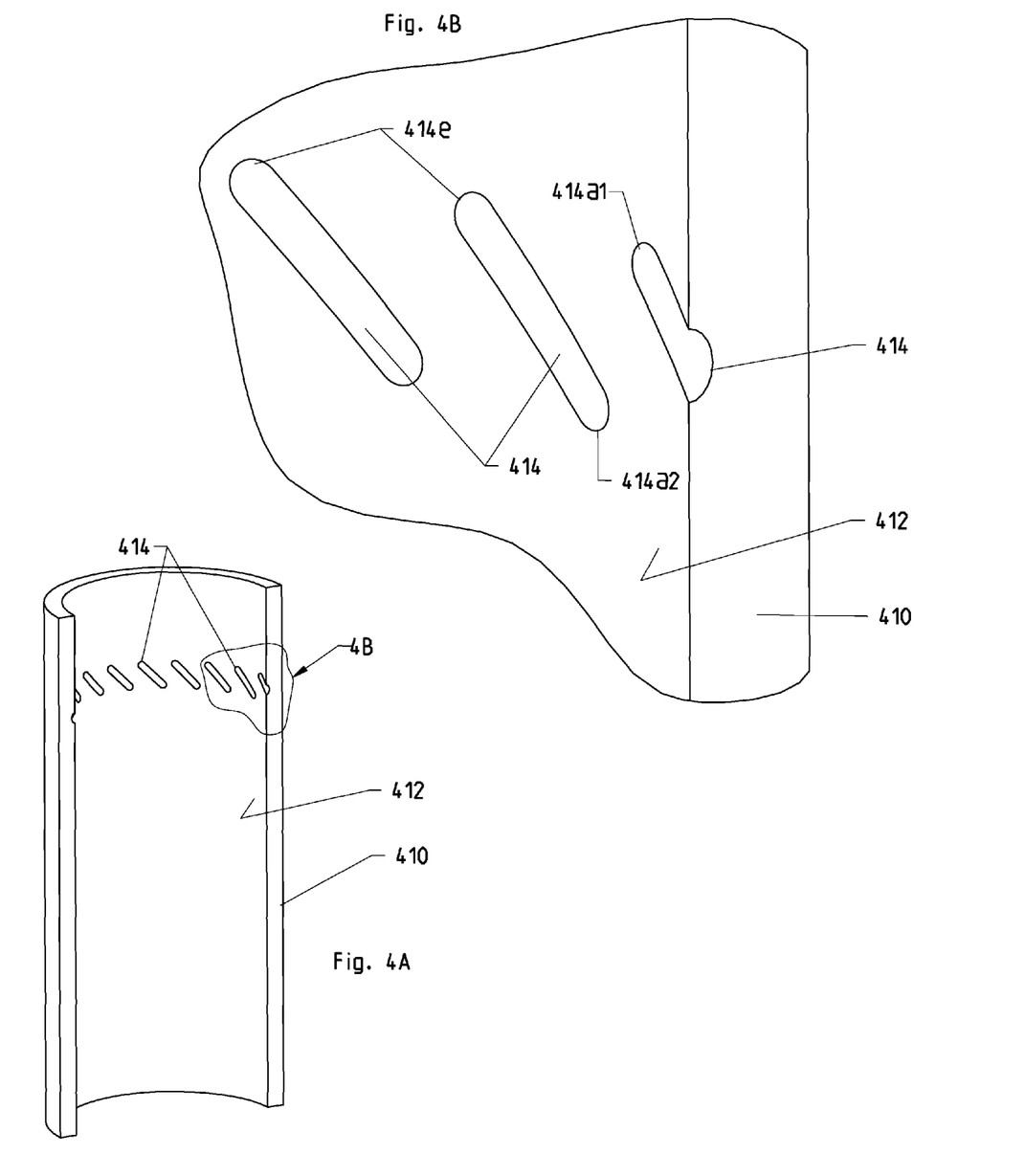
FIG. 4A is a longitudinal cross-sectional view of part of a chromatography column in accordance with the invention having angled grooves in the inner column wall.
FIG. 4B is an enlarged view of area A of FIG. 4A.

FIGS. 4A and B are longitudinal cross sectional views of part of a tubular side wall 410 of a column in accordance with the invention having diagonally orientated air grooves 414 (FIG. 4B being an enlarged view of area A of FIG. 4A). The air grooves 414 are equally spaced around the circumference of inner wall 412 but it will be understood that they may also be spaced out at varying intervals around the circumference of the wall. The air grooves 414 have smooth rounded edges or ends 414e and interior surfaces to ensure air does not become trapped inside them, but is free to move in and out. The grooves 414 are diagonally orientated or acutely angled relative to the vertical axis of the column wall 410. In the embodiment shown, the grooves 414 are positioned in such a way that one end (e.g. the upper end, $414a_1$) of one groove overlaps with the horizontal positioning of the other end (e.g. the lower end, $414a_2$) of the next groove. As described above for the vertically orientated air grooves in FIG. 3, the trapped air is forced from the bed space below the adapter assembly and moves into the diagonal grooves 414 when the movement of the adapter assembly pressurises the bed space. The diagonally orientated grooves 414 increase lateral movement of fluid into and out of the grooves and thus reduce the likelihood of any air becoming lodged or stuck within the groove.

Columns having diagonally orientated grooves in which one end of the groove does not overlap with the end of another, diagonally orientated groove, are also possible. Similarly, columns having a combination of diagonally orientated air grooves, in which the ends of some overlap and others do not, and/or combinations of vertically or axially orientated with diagonally orientated air grooves, are also possible. It will also be understood that columns having a combination of grooves which are both continuous and discrete are also possible.

Figures 5A, 5B:
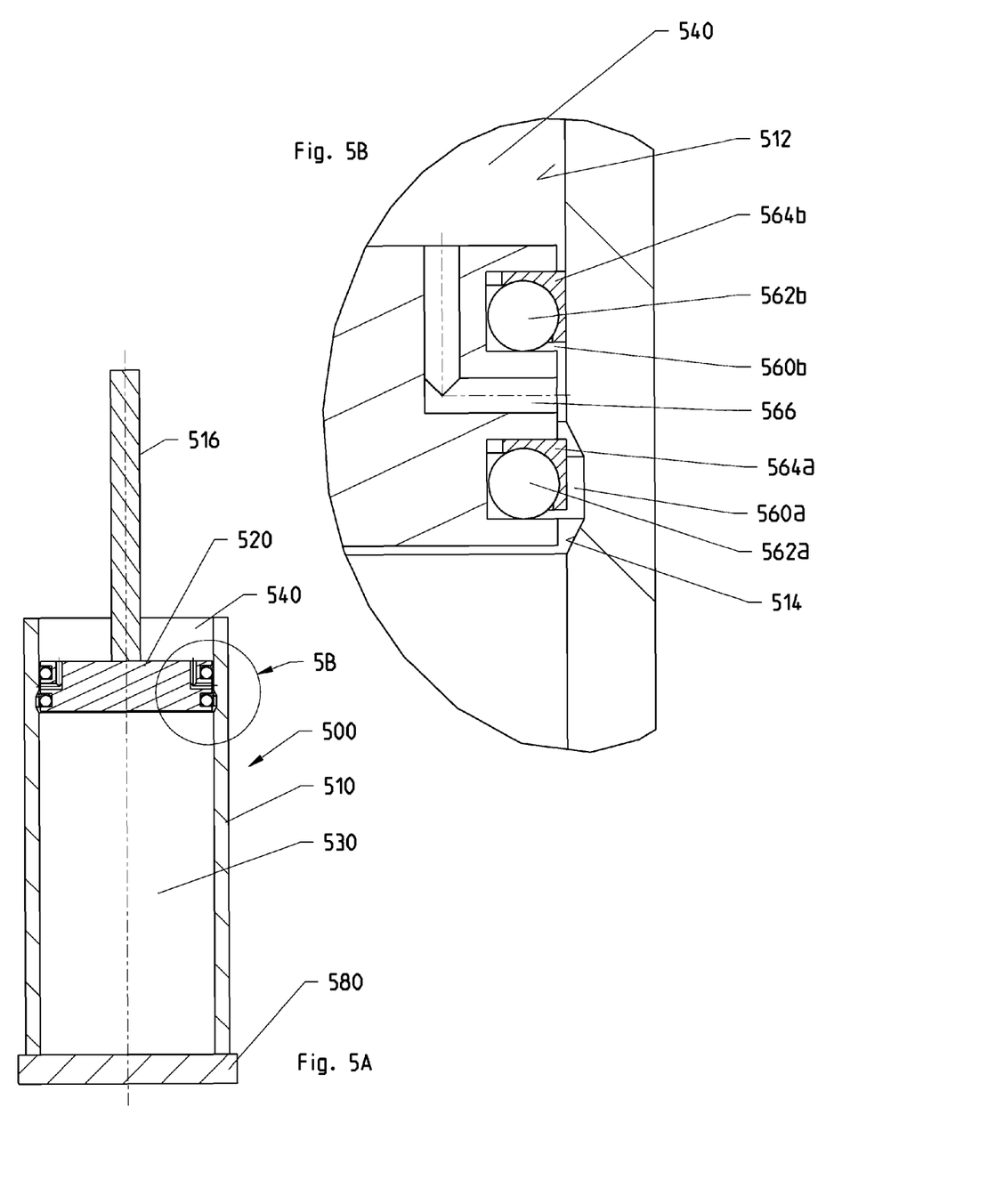
FIG. 5A is a longitudinal cross-sectional view of part of a chromatography column in accordance with the invention having two sealing assemblies.
FIG. 5B is an enlarged view of area A of FIG. 5A.

FIG. 5A is a longitudinal cross-sectional view of part of column 500 in accordance with the invention detailing the interface between the inner wall and the adapter assembly 520 incorporating two sealing assemblies 560a, b (FIG. 5B).

FIG. 5A shows the basic column components having a tubular wall 510, adapter assembly 520 and base assembly 580 forming a bed space 530 in which a bed of chromatographic media can be formed (not shown). As described in FIG. 1B, a drive shaft 516 which is connected to a suitable drive mechanism (e.g. electric motor or pneumatic pump) is used to raise and/or lower the adapter assembly 520 within the bed space 530. The adapter assembly 520 has two sealing assemblies 560a, b as shown in more detail in inset A.

Each sealing assembly 560a, b comprises an o-ring 562a, b as previously described and a separate seal 564a, b which also functions as a brush to remove particulate media from the surface of the column wall 512. The separate seal 564a, b is a circular hoop-like structure mounted on the outer edge of the o-ring 562a, b where it is supported by the o-ring 562a, b and the adapter assembly 520 in a manner that allows it a radial degree of freedom. The compressed o-ring 562a, b acts against the seal 564a, b to push it out against the column wall 512 to create a fluid-tight seal. A suitable material for the o-ring 562a, b would be a chemically resistant, durable polymer with a low surface frictional coefficient such as rubber or silicon. A suitable material for the seal 564a, b would be a TEFLON™ coated rubber or silicon as it comes into contact with the column wall 512.

The figure shows the system operating in tandem with two sealing assemblies 560a, b having o-rings 562a,b and seals 564a, b to try and minimise the loss of liquid or particulate media from the bed of particulate media present in the bed space 530.

A passage or bore 566 is present in the adapter assembly 520 which, on movement of the adapter assembly 520, can bring bed space 530 into fluid communication with chamber 540.

In operation, air is removed from the bed space 530 in the same way as described previously in FIGS. 1 and 2. The bed space 530 is filled with a slurried bed of particulate media (or priming liquid if the air should be forced out in a previous priming step as described above) to at least a level above the lowest point of the air groove 514. The adapter assembly 520 is moved axially by a drive means, such as an electric motor, to a first position where the sealing assembly 560a aligns with the air groove 514, as shown in the figure. This brings the bed space 530 into fluid communication with the chamber 540 via groove 514 and passage or bore 566, thus allowing air present in the bed space 530 to pass into the chamber 540. The adapter assembly 520 is then moved to a second position where the seal 564a is still aligned with the groove 514 in order to pressurise the bed space 530 and force air from the bed space 530 through the groove 514 and bore 566 into the chamber 540.

Alternatively, liquid is pumped from the base assembly 580 or the adapter assembly 520 into the bed space 530 to pressurise the bed space. In both cases, air present in the bed space 530 (not shown) is forced from the media bed 530 into the chamber 540 via groove 514 and bore 566.

Both sealing assemblies are independent of one another, such is their design, and it will be understood that in some embodiments of the invention only one set may be employed.

All patents, patent publications, and other published references mentioned herein are hereby incorporated by reference in their entireties as if each had been individually and specifically incorporated by reference herein. While preferred illustrative embodiments of the present invention are described, one skilled in the art will appreciate that the present invention can be practiced by other than the described embodiments, which are presented for purposes of illustration only and not by way of limitation. The present invention is limited only by the claims that follow.

What is claimed is:

1. A chromatography column comprising:
   a housing comprising an elongated tubular side wall having an inner wall; an adapter assembly and a base assembly axially opposed to each other, wherein said adapter assembly is axially movable by drive means relative to the base assembly;
   the adapter assembly and the base assembly together with said inner wall defining an enclosed bed space for containing a bed of particulate media therein;
   the adapter assembly and the inner wall defining a chamber;
   the adapter assembly includes a sealing assembly around the circumference thereof, said sealing assembly providing a fluid tight seal between the inner wall and the circumference of the adapter assembly; and
   wherein the inner wall includes at least one elongated groove for receipt of air or fluid present within the bed space.

2. The column of claim 1, wherein said elongated groove is a continuous groove around a circumference of the inner wall.

3. The column of claim 1, comprising a plurality of elongated grooves radially spaced around a circumference of the inner wall.

4. The column of claim 3, wherein said plurality of elongated grooves each has rounded edges.

5. The column of claim 3, wherein the elongated groove has a width within a range of 1 mm to 15 mm 6. The column of claim 3, wherein the elongated groove is acutely or obtusely angled relative to the vertical axis of the column.

7. The column of claim 6, wherein one end of a first groove of the plurality of elongated grooves radially overlaps with the other end of a second groove of the plurality of elongated grooves.

8. The column of claim 1, wherein the elongated groove has a depth within a range of 0.1 mm to 5 mm 9. The column of claim 1, wherein the elongated groove has a length within a range of 10 mm to 50 mm.

10. The column of claim 1, wherein the elongated groove is vertically aligned along the axis of the column.

11. The column of claim 1, wherein said sealing assembly comprises an o-ring.

12. The column of claim 1, wherein said drive means is selected from the group consisting of electrical motor, hydraulic pump and pneumatic pump.

13. A method for removing air from a chromatography column, the method comprising: providing a chromatography column according to claim 1;
   the method further comprising:
   a) filling a bed space with a bed of particulate media and/or liquid to at least a level above a lowest point of said elongated groove;
   b) axially moving the adapter assembly to a first position where the sealing assembly aligns with the elongated groove to bring the bed space into fluid communication with the chamber and thereby allow air to pass from the bed space to the chamber;

c) axially moving the adapter assembly to a second position where the sealing assembly aligns with the elongated groove and the bed space remains in fluid communication with the chamber to pressurise the bed space and thereby force air from the bed space into the chamber; and/or d) pumping a liquid from the base assembly or the adapter assembly into the bed space to force air from the bed space into the chamber.

14. The method of claim 13, further comprising axially moving the adapter assembly to a third position where the sealing assembly and the elongated groove no longer align and air cannot pass between the bed space and the chamber.

* * * * *